US008865824B2

(12) United States Patent
Bunnelle

(10) Patent No.: US 8,865,824 B2
(45) Date of Patent: Oct. 21, 2014

(54) HOT MELT ADHESIVE

(71) Applicant: IFS Industries Inc., Reading, PA (US)

(72) Inventor: William L. Bunnelle, Ham Lake, MN (US)

(73) Assignee: IFS Industries Inc., Reading, PA (US)

( * ) Notice: Subject to any disclaimer, the term of this patent is extended or adjusted under 35 U.S.C. 154(b) by 0 days.

(21) Appl. No.: 13/836,385

(22) Filed: Mar. 15, 2013

(65) Prior Publication Data

US 2014/0079919 A1 Mar. 20, 2014

Related U.S. Application Data

(60) Provisional application No. 61/702,950, filed on Sep. 19, 2012.

(51) Int. Cl.
| C08L 53/00 | (2006.01) |
| C08L 23/00 | (2006.01) |
| C08L 23/12 | (2006.01) |
| C09J 123/20 | (2006.01) |
| C08L 23/16 | (2006.01) |
| C08L 23/10 | (2006.01) |
| C08L 23/18 | (2006.01) |
| C09J 123/18 | (2006.01) |
| C08L 23/14 | (2006.01) |
| B32B 7/12 | (2006.01) |
| C09J 123/14 | (2006.01) |

(52) U.S. Cl.
CPC .............. *C09J 123/14* (2013.01); *C08L 23/12* (2013.01); *C09J 123/20* (2013.01); *C08L 23/16* (2013.01); *C08L 23/10* (2013.01); *C08L 2205/03* (2013.01); *C08L 23/18* (2013.01); *C09J 123/18* (2013.01); *C08L 2207/02* (2013.01); *C08L 23/14* (2013.01); *C08L 2205/02* (2013.01); *B32B 7/12* (2013.01)
USPC .......................................... 524/505; 525/240

(58) Field of Classification Search
USPC ........................................................ 524/505
See application file for complete search history.

(56) References Cited

U.S. PATENT DOCUMENTS

| 4,046,945 | A | 9/1977 | Baxmann et al. |
| 4,857,594 | A | 8/1989 | Lakshmanan et al. |
| 5,217,812 | A | 6/1993 | Lee |
| 5,302,675 | A | 4/1994 | Sustic et al. |
| 5,391,434 | A | 2/1995 | Krutzel |
| 5,637,665 | A | 6/1997 | Sustic et al. |
| 5,681,913 | A | 10/1997 | Sustic et al. |
| 5,685,758 | A | 11/1997 | Paul et al. |
| 5,714,554 | A | 2/1998 | Sustic et al. |
| 5,804,519 | A | 9/1998 | Riswick et al. |
| 5,998,547 | A | 12/1999 | Hohner |
| 6,143,818 | A | 11/2000 | Wang et al. |
| 6,218,457 | B1 * | 4/2001 | Fralich et al. ................. 524/489 |
| 6,281,288 | B1 | 8/2001 | Bickert et al. |
| 6,486,246 | B1 | 11/2002 | Vion |
| 6,489,400 | B2 | 12/2002 | Khandpur et al. |
| 6,582,762 | B2 | 6/2003 | Faissat et al. |
| 6,677,396 | B2 | 1/2004 | Tsui et al. |
| 6,747,114 | B2 | 6/2004 | Karandinos et al. |
| 6,767,424 | B1 | 7/2004 | Butterbach et al. |
| 6,887,941 | B2 | 5/2005 | Zhou |
| 6,992,131 | B2 | 1/2006 | Faissat et al. |
| 7,067,585 | B2 | 6/2006 | Wang et al. |
| 7,163,741 | B2 | 1/2007 | Khandpur et al. |
| 7,199,180 | B1 | 4/2007 | Simmons et al. |
| 7,262,251 | B2 | 8/2007 | Kanderski et al. |
| 7,270,889 | B2 | 9/2007 | Campbell et al. |
| 7,348,376 | B2 | 3/2008 | Gelles |
| 7,517,579 | B2 | 4/2009 | Campbell et al. |
| 7,521,507 | B2 | 4/2009 | Lewtas et al. |
| 7,524,910 | B2 | 4/2009 | Jiang et al. |
| 7,927,703 | B2 | 4/2011 | Xia et al. |
| 8,084,527 | B2 | 12/2011 | Paschkowski et al. |
| 8,193,289 | B2 | 6/2012 | Abhari et al. |
| 2004/0038058 | A1 * | 2/2004 | Zhou ............................ 428/500 |
| 2004/0204529 | A1 * | 10/2004 | Gipson ........................ 524/474 |
| 2007/0042193 | A1 | 2/2007 | Wang |
| 2007/0117894 | A1 | 5/2007 | Bach et al. |
| 2007/0117907 | A1 | 5/2007 | Bach et al. |
| 2007/0142801 | A1 | 6/2007 | Zhou et al. |
| 2007/0187032 | A1 | 8/2007 | Wang |
| 2008/0319116 | A1 | 12/2008 | Fredrickson et al. |
| 2010/0160497 | A1 | 6/2010 | Karjala et al. |
| 2011/0021102 | A1 | 1/2011 | Inoue et al. |
| 2011/0082256 | A1 | 4/2011 | Martinez et al. |
| 2011/0104508 | A1 | 5/2011 | Wang et al. |
| 2011/0167074 | A1 | 7/2011 | Heinze et al. |

(Continued)

FOREIGN PATENT DOCUMENTS

| WO | WO-02053669 | 7/2002 |
| WO | WO-2013019507 | 2/2013 |

OTHER PUBLICATIONS

"International Search Report and Written Opinion", for PCT/US2013/060660, mailed Jan. 7, 2014 (10 pages).
"Examiners Report", from AU Application No. 2013203866, mailed Jun. 28, 2013, 6 pages.
ExxonMobil Chemical, "Product datasheets for Vistamaxx", 1 page, Sep. 17, 2012.
INEOS Oligomers, "Indopol Polybutene Product Data", 2 pages, Sep. 17, 2012.
"Linxar 127 Polymer Data Sheet", ExxonMobil Chemical, Nov. 2010 (1 page).

(Continued)

*Primary Examiner* — Hui Chin
(74) *Attorney, Agent, or Firm* — Pauly, DeVries Smith & Deffner, LLC

(57) ABSTRACT

A hot melt adhesive material and articles made using the hot melt adhesive to assemble structures in an article. The adhesive material typically is manufactured by blending amorphous polymer with a heterophase polymer having crystallinity into an adhesive composition.

6 Claims, No Drawings

(56) References Cited

U.S. PATENT DOCUMENTS

| | | |
|---|---|---|
| 2012/0149827 A1 | 6/2012 | Hu et al. |
| 2012/0171466 A1 | 7/2012 | Urbach et al. |
| 2012/0178333 A1 | 7/2012 | Fowler et al. |
| 2012/0328805 A1 | 12/2012 | Davis |
| 2012/0329353 A1* | 12/2012 | Davis et al. .................. 442/381 |

OTHER PUBLICATIONS

"REXtac LLC, Advance Technology", 1990, 2 pages.

"Vistamaxx 2330 Propylene-based Elastomer", ExxonMobil Chemical, Last updated: Jan. 26, 2011, http://prospector.ides.com/DataView.aspx?E=114449 (2 pages).

* cited by examiner

HOT MELT ADHESIVE

Disclosed is a general purpose hot melt adhesive material that can be applied to substrates such as cellulosic materials, film, fiber or nonwovens in the construction of articles. The adhesive composition is manufactured to obtain melt viscosity, cohesion and adhesion sufficient to assemble an article and obtain a mechanically stable product. The adhesive typically comprises a blend of polymer materials combined at proportions that obtain the desired and useful construction properties useful in the manufacture of articles. One embodiment is the hot melt adhesive. A second embodiment is an article manufactured using the construction properties and aspects of the hot melt adhesive.

Common hot melt adhesives are made by combining polymer and additive components in a substantially uniform thermoplastic blend. Improved materials are needed for use in improved application equipment and in current and updated article constructions. A substantial need exists in providing new formulation combinations of materials and blending techniques that obtain improved adhesives.

The adhesive composition comprises a first amorphous polymer and a second heterophase polymer. The amorphous polymer comprises an amorphous or random polymer comprising an alpha olefin co-polymer comprising major proportion of propene. The second polymer comprises a heterophase alpha olefin-co-polymer having amorphous character and at least some substantial crystalline content. The crystalline content can be in the form of one or more polymer blocks or sequences that are stereoregular. In one embodiment, these sequences or blocks are substantially crystallizable sequences or blocks.

As used herein "homopolymer" means a polymer resulting from the polymerization of a single monomer, i.e., a polymer consisting essentially of a single type of repeating unit.

As used herein, the term "copolymer(s)" refers to polymer(s) formed by the polymerization of at least two different monomers. For example, the term "copolymer" includes the copolymerization reaction product of a monomer such as propene or butene, preferably 1-butene and an α-olefin, such as for example, ethylene, 1-hexene or 1-octene.

As used herein, the term "propene copolymer" or "propylene copolymer" means a copolymer of greater than 40 or 50 wt. % or more propene and at least one monomer selected from the group including ethylene and a $C_4$ to $C_{20}$ α-olefin.

As used herein, the term "butene copolymer" means a polymer of n-butene (1-butene) or 2-butene and at least one monomer selected from the group of $C_{2-3}$ and $C_{5-20}$ alpha olefins. Butene copolymers typically comprise a minimum amount at least about 40 or about 50 wt. % or more of a butene monomer such as 1-butene.

The term "heterophase" polymer means a polymer having an amorphous character and at least some substantial crystalline content (at least 5 wt. %, 10 wt. %, 20 wt. %, 40 wt. % or 50 wt. % crystalline content) that can provide cohesive strength in the cooled adhesive mass. The crystalline content can be in the form of stereoregular blocks or sequences.

The term "amorphous" means the substantial absence of crystallinity, (i.e.) less than 5% and less than 1%.

The term "sequence or block" means a polymer portion of repeating monomer that is similar in composition, crystallinity or other aspect.

As used herein, the term "open time" means the amount of time elapsed between application of a molten hot melt adhesive composition to a first substrate, and the time when useful tackiness or wetting out of the adhesive on a substrate effectively ceases due to solidification of the adhesive composition. Open time is also referred to as "working time."

As used herein, the term "substrate" means any item having at least a partially or fully solidified fiber or planar surface with which contact with a hot melt adhesive composition is intended. In some cases the same area, circle, bead, line, filament or dot of hot melt adhesive composition is contacted with two or more substrates for the purpose of creating an adhesive bond there between. In some such cases the substrates are part of the same item: for example, folded film or folded non-woven, two sides of a cardboard sheet folded over, wherein the two sides are adhesively bonded together. In other such cases the substrates are part of different items: for example, a plastic film that is adhesively bonded to a non-woven or cardboard sheet. The substrates can be impermeable, permeable, porous or nonporous.

As used herein, the term "substantially" means generally the same or uniform but allowing for or having minor fluctuations from a defined property, definition, etc. For example, small measurable or immeasurable fluctuations in a measured property described herein, such as viscosity, melting point, etc. may result from human error or methodology precision. Other fluctuations are caused by inherent variations in the manufacturing process, thermal history of a formulation, and the like. The adhesive compositions of the, nonetheless, would be said to be substantially having the property as reported.

As used herein, the term "major proportion" means that a material or monomer is used at greater than 50 wt. %. As used herein, the term "primary component" means that a material or monomer is the more common substance or has the higher concentration in the mixture or polymer compared to others but may not be as much as 50 wt. %.

The adhesive material comprises a first polymer comprising a polyolefin comprising a substantially amorphous or randomly polymerized polymer material and a second polymer comprising a heterophase polymer.

The first amorphous polymer comprises typically butene (e.g.) 1-butene and can contain ethylene, propene or a second $C_{4\text{-}40}$ olefin polymer. These substantially amorphous low crystallinity polymers have less than 10% and preferably less than 5% crystalline character.

The second heterophase olefin polymer comprises a first poly alpha olefin polymer comprising a substantial proportion (greater than 40 or 50 mole %) of a propene monomer and comprises an amorphous polymer with some crystalline content.

The amorphous polymer is a butene-based copolymer (the minimum amount is at least about 30 or 40 or 50 wt. % of 1-butene), which may also be referred to as a random butene-α-olefin copolymer. The butene copolymer includes one or more units, i.e., mer units, derived from propene, one or more comonomer units derived from ethylene or α-olefins including from 4 to about 20 carbon atoms.

The first copolymer comprises about 30 mole %-about 70 mole %, preferably about 40 mole % to about 60 mole % of units derived from butene. In addition to butene-derived units, the present copolymer contains from about 70 mole %-about 30 mole % to about 60 mole %-about 40 mole %, of units derived from preferably ethylene, propene or at least one $C_{5\ to\ 10}$ alpha-olefin monomer.

In one or more embodiments, the α-olefin comonomer units can also be derived from other monomers such as ethylene, 1-butene, 1-hexene, 4-methyl-1-pentene and/or 1-octene. Exemplary alpha-olefins are selected from the group consisting of ethylene, butene-1, pentene-1,2-methylpentene-1,3methylbutene-1, hexene-1,3-methylpentene-1,4- methylpentene-1,3,3-dimethylbutene-1, heptene-1, hexene-1, methylhexene-1, dimethylpentene-1, trimethylbutene-1, ethylpentene-1, octene-1, methylpentene-1, dimethylhexene-1, trimethylpentene-1, ethylhexene-1, methylethylpentene-1, diethylbutene-1, propylpentane-1, decene-1, methylnonene-1, nonene-1, dimethyloctene-1, trimethylheptene-1, ethyloctene-1, methylethylbutene-1, diethylhexene-1, dodecene-1, and hexadodecene-1.

In one or more embodiments, amorphous copolymer comprises about 30 mole %-about 70 mole %, preferably about 40 mole % to about 60 mole % of units derived from butene and from about 70 mole %-about 30 mole % to about 60 mole %-about 40 mole %, of units derived from at least one alpha-olefin monomer selected from ethylene, propene, 1-hexene or 1-octene. Small amounts of α-olefin monomer(s) can be used in the range of about 0.1 to 20 mole %. The amorphous polymer has a weight average molecular weight (Mw) of about 1,000 to about 25,000 or less, preferably about 2,000 to 20,000.

In one or more embodiments, first copolymer comprises about 30 mole %-about 70 mole %, preferably about 40 mole % to about 60 mole % of units derived from butene and from about 70 mole %-about 30 mole % to about 60 mole %-about 40 mole %, of units derived from propene, while small amounts of α-olefin monomer(s) can be used in the range of about 0.1 to 20 mole %.

The amorphous polymer has a weight average molecular weight (Mw) of about 1,000 to about 50,000 or less, preferably about 5,000 to 45,000. The amorphous copolymer has a viscosity of less than 10,000 mPa·s (1 centipoise [cps]=1 mPa·s), for example about 2000 to 8000 mPa·s, when measured by ASTM D3236 at 190° C. Melt Viscosity was determined according to ASTM D-3236, which is also referred to herein as "viscosity" and/or "Brookfield viscosity".

Some examples of amorphous polyolefin include the Rextac polymers made by Huntsman including Rextac E-63, E-65, 2815, 2830, etc. See, for example Sustic, U.S. Pat. No. 5,723,546 for a description of the polymers and which is expressly incorporated herein. Other useful amorphous polymers are sold as Vistoplast® and Eastoflex® materials.

The adhesive material comprises a second polyolefin comprising a substantially heterophase copolymer. The heterophase polyolefin may comprise a propene copolymer (i.e.) propene-based polymer with other comonomer(s). The propene-based polymer backbone preferably comprises propene and one or more $C_2$ or $C_{4-20}$ α-olefins. The propene-based heterophase polymer, for example, may comprise propene and ethylene, hexene or optionally other $C_2$ or $C_{4-20}$ α-olefins. The polymer comprises about 99.5 to about 70 wt. %, preferably about 95 to about 75 wt. % of units derived from propene. In addition to propene derived units, the present copolymer contains from about 0.1 to 30 wt. % preferably from about 5 to 25 wt. %, of units derived from preferably at least $C_{2-4}$ or a $C_{5-10}$ alpha-olefin.

In one or more embodiments, the second copolymer comprises a major proportion of propene and about 0.1 to 30 wt. %, or 2 to 25 wt. % ethylene. In one or more embodiments, the second copolymer comprises a major proportion of propene and about 0.1 to 30 wt. %, or 2 to 25 wt. % 1-butene.

In one or more embodiments, the second copolymer comprises a major proportion of propene and about 0.1 to 30 wt. %, or 2 to 25 wt. % 1-hexene. In one or more embodiments, the second copolymer comprises a major proportion of propene and about 0.1 to 30 wt. %, or 2 to 25 wt. % 1-octene.

Other comonomer for use in either the first or second polyolefin comprise ethylene or α-olefins containing 4 to 12 carbon atoms. Exemplary α-olefins may be selected from the group consisting of ethylene; 1-butene; 1-pentene; 2-methyl-1-pentene; 3-methyl-1-butene; 1-hexene-3-methyl-1-pentene-4-methyl-1-pentene-3,3-dimethyl-1-butene; 1-heptene; 1-hexene; 1-methyl-1-hexene; dimethyl-1-pentene; trimethyl-1-butene; ethyl-1-pentene; 1-octene; methyl-1-pentene; dimethyl-1-hexene; trimethyl-1-pentene; ethyl-1-hexene; 1-methylethyl-1-pentene; 1-diethyl-1-butene; propyl-1-pentene; 1-decene; methyl-1-nonene; 1-nonene; dimethyl-1-octene; trimethyl-1-heptene; ethyl-1-octene; methylethyl-1-butene; diethyl-1-hexene; 1-dodecene and 1-hexadodecene. Preferred $C_{4-10}$ alpha-olefins are those having 6 to 8 carbon atoms, with the most preferred alpha-olefin being 1-hexene and 1-octene.

Preferred propene copolymers are copolymers wherein the comonomer is ethylene, 1-butene, 1-hexene or 1-octene. The stereo-regular (isotactic or syndiotactic) sequence or block content of the polymers imparts a heterophase (partial amorphous and partial crystalline) character of crystallizable content to the polymers. As used herein and as applied to semicrystalline heterophase copolymers, the term "crystallizable" describes those polymer sequences or blocks that can crystallize upon cooling. Crystalline content of the solidified semicrystalline copolymers increases the cohesive strength of the hot melt adhesives. Hot melt adhesive formulations based on metallocene polymerized semicrystalline copolymers can eventually build sufficient crystalline content over time to achieve good cohesive strength in the formulation.

The second heterophase polymer comprises crystallizable polymer blocks or sequences, preferably of stereoregular sequences of polymerized monomer such as ethylene or propene, which sequences are long enough to crystallize, typically at least repeating or block monomer units per sequence.

In preferred embodiments, the crystallizable segments can be stereoregular or isotactic. Isotacticity of the olefin sequences can be achieved by polymerization with the choice of a desirable catalyst composition. The Isotacticity is conventionally measured using DSC or C-13 NMR instrumental techniques.

The heterophase polymer has a crystallinity of at least 5 wt. %, 10 wt. %, 20 wt. %, 40 wt. % or 50 wt. %, preferably between 20% and 80%, more preferably between 25% and 70%.

The heat of fusion of the heterophase copolymers (by ASTM E793) is about 10 J/g to about 70 J/g and about 15 J/g to about 70 J/g, with a melting point less than 150° C. and about 105° C. to about 135° C.

The heterophase polymer has a weight average molecular weight (Mw) of about 20,000 or less, preferably about 10,000 or less, preferably about 500 to 8,000.

The heterophase copolymer has a viscosity of less than 20,000 mPa·s (1 centipoise [cps]=1 mPa·s), for example less than 15000 mPa·s, in certain application less than 10,000 mPa·s and less than 5,000 mPa·s when measured at 190° C. using a Brookfield viscometer (as measured by ASTM D 3236) which is also referred to herein as "viscosity" and/or "Brookfield viscosity."

Some examples of heterophase polymers useful in the hot melt adhesive compositions of include polyolefin such as polyethylene, polypropylene, and copolymers thereof such as polypropylene based elastomers sold by ExxonMobil Chemical of Houston, Tex. under the trade name VISTAMAXX™ and polyethylene based elastomers such as those sold by Dow Chemical Company of Midland, Mich. under the trade names AFFINITY™ and ENGAGE™.

Other heterophase polymers that are useful in the hot melt adhesive compositions include the polyolefin elastomers VISTAMAXX™ 8816, VISTAMAXX™ 2230, and ENGAGE™ 8200. AFFINITY™ GA 1900 has a density of 0.870 g/cm³ according to ASTM D792, heat of fusion of 46.1 J/g, and a Brookfield viscosity of 8200 cP at 177° C. according to ASTM D 1084. AFFINITY™ GA 1950 has a density of 0.874 g/cm³ according to ASTM D792, heat of fusion of 53.4 J/g, and a Brookfield viscosity of 17,000 cP at 177° C. according to ASTM D 1084. ENGAGE™ 8200 has a density of 0.87 g/cm³ according to ASTM D792 and a melt index of 5 g/10 min at 190° C. These olefin elastomers are compatible with the propylene copolymers useful in the hot melt adhesive compositions and improve physical properties such as low temperature adhesive performance without sacrificing effective set time.

Any conventional polymerization synthesis processes may prepare the polyolefin copolymers. Preferably, one or more catalysts, which are typically metallocene catalysts or Zeigler-Natta, catalysts, are used for polymerization of an olefin monomer or monomer mixture. Polymerization methods include high pressure, slurry, gas, bulk, suspension, supercritical, or solution phase, or a combination thereof, preferably using a single-site metallocene catalyst system. The catalysts can be in the form of a homogeneous solution, supported, or a combination thereof. Polymerization may be carried out by a continuous, a semi-continuous or batch process and may include use of chain transfer agents, scavengers, or other such additives as deemed applicable. By continuous is meant a system that operates (or is intended to operate) without interruption or cessation. For example a continuous process to produce a polymer would be one where the reactants are continually introduced into one or more reactors and polymer product is continually withdrawn. In one embodiment, the propene copolymer described herein is produced in a single or multiple polymerization zones using a single polymerization catalyst. The heterophase polymers are typically made using multiple metallocene catalyst blends that obtain desired heterophase structure.

The compositions disclosed herein can also comprise a plasticizer or plasticizing oil or extender oil that may reduce viscosity or improve tack properties in the adhesive. Any plasticizer known to a person of ordinary skill in the art may be used in the adhesion composition disclosed herein. Non-limiting examples of plasticizers include olefin oligomers, low molecular weight polyolefin such as liquid polybutene, low molecular weight non-aromatic polymers (e.g. REGAL-REZ 101 from Eastman Chemical Company), phthalates, mineral oils such as naphthenic, paraffinic, or hydrogenated (white) oils (e.g. Kaydol oil or ParaLux oils (Chevron U.S.A. Inc.)), vegetable and animal oil and their derivatives, petroleum derived oils, and combinations thereof. Low molecular weight polyolefin may include those with Mw as low as 100, in particular, those in the range of from about 100 to 3000, in the range of from about 250 to about 2000 and in the range of from about 300 to about 1000.

In some embodiments, the plasticizers include polypropylene, polybutene, hydrogenated polyisoprene, hydrogenated polybutadiene, polypiperylene, copolymers of piperylene and isoprene, and the like, having average molecular weights between about 350 and about 10,000. In other embodiments, the plasticizers include glyceryl esters of the usual fatty acids and polymerization products thereof a polymer of isobutylene. A preferred plasticizer comprises a polyisobutylene polymer. The polymer can comprise major proportion of isobutylene units or can be represented as:

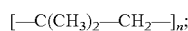

wherein n=15 to 75. Polyisobutylene materials are viscous liquids with molecular weight of about 200-20,000, about 200-5,000 or about 500-2,000. The preferred materials have a Saybolt Universal seconds (SUS) viscosity at 100° C. of about 100 to 20,000. The characteristic features of polyisobutylene are low gas permeability and high resistance to the action of acids, alkalis, and solutions of salts, as well as high dielectric indexes. They degrade gradually under the action of sunlight and ultraviolet rays (the addition of carbon black slows this process). In industry, polyisobutylene is produced by ionic (AlCl₃ catalyzed) polymerization of the monomer at temperatures from −80° to −100° C.; they are processed using the ordinary equipment of the rubber industry. Polyisobutylene combines easily with natural or synthetic rubbers, polyethylene, polyvinyl chloride, and phenol-formaldehyde resins.

As noted above, embodiments of preferred compositions are made with substantially less than 40 wt. %, less than 20 wt. % or are substantially free of an effective amount of a conventional tackifier material that can add any aspect of open time, substrate wetting or tack to the adhesive material. Avoiding the use of a tackifier reduces adhesive density, adhesive and product costs and frees formulators from the use of materials in short supply. Further, tackifier can impart undesirable odor in disposable articles and can also act as carriers of low molecular weight plasticizers (like process oils that are used in SBC based adhesives) that can weaken the polyethylene back sheet materials used in baby diapers. Back sheet integrity is becoming more important due to the downsizing of the polyethylene film thickness used in these articles. By the term "conventional tackifier resins", those resins commonly available in the adhesive art and industry that are used in typical hot melt adhesives. Examples of conventional tackifing resins included in this range include an aliphatic hydrocarbon resins, aromatic modified aliphatic hydrocarbon resins, hydrogenated poly-cyclopentadiene resins, poly-cyclopentadiene resins, gum rosins, gum rosin esters, wood rosins, wood rosin esters, tall oil rosins, tall oil rosin esters, poly-terpene, aromatic modified poly-terpene, terpene-phenolic, aromatic modified hydrogenated poly-cyclopentadiene resins, hydrogenated aliphatic resins, hydrogenated aliphatic aromatic resins, hydrogenated terpene and modified terpene and hydrogenated rosin esters. Often in conventional formulations such resins are used in amounts that range from about 40 to about 65 wt. %.

In further embodiments, the compositions disclosed herein optionally can comprise an antioxidant or a stabilizer. Any antioxidant known to a person of ordinary skill in the art may be used in the adhesion composition disclosed herein. Non-limiting examples of suitable antioxidants include amine-based antioxidants such as alkyl diphenyl amines, phenyl-naphthylamine, alkyl or aralkyl substituted phenyl-naphthylamine, alkylated p-phenylene diamines, tetramethyl-diaminodiphenylamine and the like; and hindered phenol compounds such as 2,6-di-t-butyl-4-methylphenol; 1,3,5-trimethyl-2,4,6-tris(3',5'-di-t-butyl-4'-hydroxybenzyl)benzene; tetra kis[(methylene(3,5-di-t-butyl-4-hydroxyhydrocinnamate)]methane (e.g., IRGANOX™1010, from Ciba Geigy, New York); octadecyl-3,5-di-t-butyl-4-hydroxycinnamate (e.g., IRGANOX™ 1076, commercially available from Ciba Geigy) and combinations thereof. Where used, the amount of the antioxidant in the composition can be from about greater than 0 to about 1 wt. %, from about 0.05 to about 0.75 wt. %, or from about 0.1 to about 0.5 wt. % of the total weight of the composition.

In further embodiments, the compositions disclosed herein optionally can comprise an UV stabilizer that may prevent or reduce the degradation of the composition by radiation. Any UV stabilizer known to a person of ordinary skill in the art may be used in the adhesion composition disclosed herein. Non-limiting examples of suitable UV stabilizers include benzophenones, benzotriazoles, aryl esters, oxanilides, acrylic esters, formamidine carbon black, hindered amines, nickel quenchers, hindered amines, phenolic antioxidants, metallic salts, zinc compounds and combinations thereof. Where used, the amount of the UV stabilizer in the composition can be from about greater than 0 to about 1 wt. %, from about 0.05 to about 0.75 wt. %, or from about 0.1 to about 0.5 wt. % of the total weight of the composition.

In further embodiments, the compositions disclosed herein optionally can comprise a brightener, colorant or pigment. Any colorant or pigment known to a person of ordinary skill in the art may be used in the adhesion composition disclosed herein. Non-limiting examples of suitable brighteners, colorants or pigments include fluorescent materials and pigments such as triazine-stilbene, coumarin, imidazole, diazole, titanium dioxide and carbon black, phthalocyanine pigments, and other organic pigments such as IRGAZINB, CROMOPHTALB, MONASTRALB, CINQUASIAB, IRGALITEB, ORASOLB, all of which are available from Ciba Specialty Chemicals, Tarrytown, N.Y. Where used, the amount of the brightener, colorant or pigment in the composition can be from about greater than 0 to about 10 wt %, from about 0.01 to about 5 wt %, or from about 0.1 to about 2 wt % of the total weight of the composition.

The compositions disclosed herein may also optionally comprise a fragrance such as a perfume or other odorant. Such fragrances may be retained by a liner or contained in release agents such as microcapsules that may, for example, release fragrance upon removal of a release liner from or compression on the composition.

In further embodiments, the compositions disclosed herein optionally can comprise filler. Any filler known to a person of ordinary skill in the art may be used in the adhesion composition disclosed herein. Non-limiting examples of suitable fillers include sand, talc, dolomite, calcium carbonate, clay, silica, mica, wollastonite, feldspar, aluminum silicate, alumina, hydrated alumina, glass bead, glass microsphere, ceramic microsphere, thermoplastic microsphere, barite, wood flour, and combinations thereof. Where used, the amount of the filler in the composition can be from about greater than 0 to about 60 wt. %, from about 1 to about 50 wt. %, or from about 5 to about 40 wt. %

TABLE 1

Exemplary and Useful Substantially Tackifier Free Adhesive Compositions

| Component | Embodiment | Wt. % | Wt. % | Wt. % |
|---|---|---|---|---|
| Amorphous polymer | REXTAC E65 | 90-10 | 20-80 | 70-40 |
| Heterophase polymer | Vistamaxx | 10-90 | 80-20 | 40-70 |
| Plasticizer | Polyisobutylene | 0-40 | 5-35 | 5-30 |
| Additive | Antioxidant/stabilizer | 0-20 | 1-20 | 1-15 |

One substantial advantage in the claimed adhesives relates to a density of the adhesive formulations. Conventional tackifier is at a density that often ranges from about 1.07-1.09 g-cm$^{-3}$. Conventional formulated adhesives containing a conventional tackifier in amounts of about 40 to 60 wt. %, have a density greater than 0.9 g-cm$^{-3}$ or more. The formulated adhesives of the invention, substantially free of tackifier, have densities less than 0.9 g-cm$^{-3}$, often in the range about 0.85-0.89 g-cm$^{-3}$ often 0.86-0.87 g-cm$^{-3}$. Not only are these adhesives free of the problems arising from tackifier materials, but the use of the claimed adhesives, and a lower density, permits the use of a reduced amount when measured by weight, resulting in cost savings.

The hot melt adhesive compositions have melt rheology and thermal stability suitable for use with conventional hot melt adhesive application equipment. The blended components of the hot melt adhesive compositions have low melt viscosity at the application temperature, thereby facilitating flow of the compositions through a coating apparatus, e.g., coating die or nozzle, without resorting to the inclusion of solvents or extender oil into the composition. Melt viscosities of the hot melt adhesive compositions are between 1500 cP and 3500 cP or about 2000 cP to 3000 cP in mille Pascal-seconds or centipoise (cP) using a Brookfield thermosel RVT viscometer using a rotor number 27 at 176.66° C. (50 rpm, 350° F.). The hot melt adhesive compositions have a softening point (ASTM D 3461-97 Standard Test Method for Mettler Softening Point Method) of about 80° C. to 140° C., in some embodiments about 115° C. to 130° C. For certain applications, the hot melt adhesive compositions have effective set times of about 5 seconds or less, for example about 0.1 second to 5 seconds, in embodiments about 0.1 second to 3 seconds, and in some embodiments about 0.2 second to 1 second. The effective set time of the hot melt adhesives are unexpectedly short, particularly given that the open time remains in the acceptable range.

Typical but non-limiting industrial applications of the hot melt adhesive compositions include packaging, particularly for low temperature use such as for dairy products or for freezer packaging of food products, and in sanitary disposable consumer articles, for example, diapers, feminine care pads, napkins, etc. Traditional end use applications such as book-binding, wood working and labeling will also benefit from both the low temperature flexibility, heat resistance and the efficiency of end use in automated means of applying the hot melt adhesive compositions to various substrates.

Articles include items having any two or more substrates adhesively bonded by a hot melt adhesive composition. Articles include cartons, boxes, envelopes, comestibles containers, books, magazines, disposable articles such as diapers or feminine napkins, and the like. The substrates that are adhesively bonded in such articles are formed from materials such as cardboard, paper, wood, aluminum, tin, steel, thermoplastics such as polyesters such as polyethylene terephthalate, polyamides such as nylons, or polypropylene, thermoset polymers, glass, ceramics, and combinations, blends, or layered composites thereof and include, in some embodiments, coatings of wax, acrylate polymers, or other materials; colorants, preservatives, stabilizers, processing lubricants, and the like as well as combinations of any of these materials. The substrates include solid, nonporous items and sheets as well as porous items and sheets, such as nonwoven fabrics, paper, cotton batting, and the like.

Another aspect is methods of manufacture employing the hot melt adhesive compositions. The method involves application of the molten compositions to a substrate, followed by contact of the adhesive composition with a second substrate within 0.1 second to 5 seconds after application of the adhesive composition to the first substrate, wherein the contacting results in an adhesive bond between the substrates.

Yet another aspect is an article of manufacture including the hot melt adhesive compositions, wherein the article includes at least two substrates adhesively bonded by an amount of a hot melt adhesive composition. Typical articles of manufacture include packaged goods, particularly packaged goods intended for low temperature use such as in dairy products or for freezer packaging of food products; sanitary disposable consumer articles, for example, diapers, feminine care pads, napkins, and the like; books and magazines; labeled articles; wood articles such as furniture; and articles formed from a combination of low energy and higher energy materials, for example a cardboard box having a polyethylene wrap and/or a polypropylene label, or a wood frame table having a protective plastic top. In general, articles that are advantageously bonded using the hot melt adhesive compositions benefit from both the low temperature flexibility, heat resistance and the efficiency of end use in automated means of applying the adhesive compositions to substrates.

Hot melt adhesive compositions were formulated by melt blending as described below, wherein specific components and amounts of the components are shown below. In the articles manufactured using the adhesives, the articles can be manufactured by forming an adhesive bond between a polymer film and a fiber or fiber mass. The article can also comprise an adhesive bond formed between a polymer film and a nonwoven fabric. Additionally the article can be manufactured by forming an adhesive bond between a multi layer structure comprising the exterior layer of a polymer film and interior components comprising a fiber map or a nonwoven fabric.

The adhesive materials can be used as a construction adhesive in assembly of commonly available consumer disposal articles. Such articles include infant diapers, adult diapers, bed pads, sanitary products, and other absorbent articles. Combining at least a polymer film with other films and fibrous materials typically makes these articles. Fibrous materials can include fabrics such as woven or nonwoven fabrics, fibers in the form of fiber vats, fiber collections, fiber balls, etc.

Such absorbent articles typically comprise an absorbent held within the article. The absorbent is usually covered using a nonwoven inner liner. Such liners comprise a highly permeable material such as a spunbonded nonwoven structure that passes fluids or moisture from the interior of the article into the absorbent layer. The absorbent layer or structure formed within the absorbent article typically comprises a fiber mass pad or cellulosic or wood pulp for the purpose of substantially absorbing liquid or fluid materials released into the absorbent article. The fiber or fluff can comprise a cellulosic fiber, a synthetic fiber or mixtures thereof such as blends of wood fiber, cellulosic fiber, polyethylene fiber, polypropene fiber or other fiber materials often including a super absorbent material. Super or highly absorbent materials are used to increase the absorptive capacity of the absorbent article. Such materials are organic materials including modified natural gums and resins but often include synthetic polymer materials such as hydrogels. Carboxy-methyl Cellulose, alkaline metal salts of acrylic polymers, polyacrylamides, polyvinyl alcohol, polyethylene anhydride polymers and copolymers, polyvinyl ether polymers and copolymers, hydroxyalkyl cellulose polymers and copolymers, polyvinyl sulfonic acid polymers and copolymers, polyacrylic polymers, polyvinyl-pyrrolidone polymers and copolymers can be used in the absorbent function.

Nonwoven fabric layers used in such disposal articles typically are generally planar structures comprising a bonded assembly of natural or synthetic fiber.

Such nonwoven materials are often made using a variety of techniques, including spunbonding, melt bonding, etc. Such nonwoven materials are often manufactured by randomly placing fibers or rovings in a substantially random pattern and are then thermally bonded using inherent bonding characteristics of the fibers or by bonding the fibers using resin materials applied to the fibers. Various polymers can be used to make nonwoven materials including poly olefins, polyesters, ethylene vinyl acetate polymers, ethylene acrylic acid polymers and others.

The exterior of the article often comprises a polymer film that is liquid impervious. In certain aspects exterior polymer films can be further modified using additional exterior layers to obtain a more cloth like or nonwoven character to the exterior polymer film. The exterior film typically comprises a single layer of a polymer film but can be a multi-layer film structure. Typical polymer sheet materials comprise high tensile strength polymers including polyesters, poly olefins or other thermoplastic sheet materials that can be formed into film layers. The polyolefin or polyester polymer materials are often formed into sheets and are treated to improve strength, flexibility and puncture resistance. Techniques including biaxial orientation, heat treatment or surface treatment can improve the film characteristics of the polymer films. Such polymer films often have a thickness that ranges from about ten to about one hundred microns.

One embodiment of an absorbent article that we have mentioned comprises the impervious polymer film, an absorbent layer pad or mat and a nonwoven interior layer. This three component structure is assembled using the adhesive that is applied using manufacturing techniques that adheres the nonwoven interior layer to the polymer film while holding the absorbent layer there between.

The adhesive compositions can be applied under melt conditions to a substrate as a hot melt adhesive or may be coated, applied or sprayed onto the polymer film nonwoven or absorbent pad. Spray-on adhesives are typically applied using slot coat, spray on or atomizing character in a bead, dot pattern, spiral pattern or other conventional pattern using such Nordson application techniques. In a preferred embodiment, the composition of the adhesive composition is applied to a substrate using a slot coat (using Nordson true coat or Speed coat slot) at increased machine speed.

The material is typically applied in an amount of about 1 to about 100 or about 4 to about 90 or about 7 to about 70 grams per square meter ($g\text{-}m^{-2}$) of resulting bonded material. The adhesive materials can be used for disposal diaper and napkin construction elastic attachment and disposal goods particularly preferred applications include baby diaper construction, diaper chassis construction, diaper core stabilization, diaper outer cover lamination, feminine napkin core stabilization, feminine napkin adhesive strip.

EXPERIMENTAL

A number of hot melt adhesive compositions were prepared by blending first amorphous copolymer, second heterophase copolymer, polymer plasticizer/diluent and antioxidant under mixing conditions at elevated temperatures to form a fully homogenized fluid melt. Mixing temperatures varied from about 135 to about 200° C. preferably about 150 to about 175° C. A WiseStir® mixer was used to ensure full homogenization of components into a final adhesive composition.

Examples 1-4

Hot melt adhesive compositions were formulated by melt blending as described below, wherein specific components and amounts of the components are shown in the following table 2.

TABLE 2

Exemplary Adhesive Formulations

| Source | Component | Ex. 1 wt. % | Ex. 2 wt. % | Ex. 3 wt. % | Ex. 4 wt. % | Ex. 5 wt. % | Ex. 6 wt. % | Ex. 7 wt. % | Ex. 8 wt. % |
|---|---|---|---|---|---|---|---|---|---|
| ExxonMobil Chemical, Houston, TX | Vistamaxx 8816 | 20 | 35 | 35 | 35 | 15 | 15 | 15 | 10 |
| Huntsman Chemicals | Rextac E-65 | 59.5 | 60 | 55 | 50 | 64.5 | 59.5 | 59.5 | 59.5 |
| Ineos Chemicals | Indapol H-300 (polyisobutylene) (Polyisobutylene) | 20 | 4.5 | 9.5 | 14.5 | 20 | 24.99 | 0 | 0 |
| Ineos Chemicals | Indapol H-1900 (Polyisobutylene) | 0 | 0 | 0 | 0 | 0 | 0.5 | 24.99 | 29.99 |
| Ciba Geigy Ltd., Basel, Switzerland | Irganox 1010 (Hindered Phenol) | 0.5 | 0.5 | 0.5 | 0.5 | 0.5 | 0.5 | 0.5 | 0.5 |
| Mayzo, Inc. Fluorescent Optical Brightener | Benetex OB | 0 | 0 | 0 | 0 | 0 | 0.01 | 0.01 | 0.01 |

TABLE 3

EXEMPLARY ADHESIVE VISCOSITY DATA

| Brookfield Viscosity @ | Ex. 1 | Ex. 2 | Ex. 3 | Ex. 4 | Ex. 5 | Ex. 6 | Ex. 7 | Ex. 8 |
|---|---|---|---|---|---|---|---|---|
| 121.1° C. (250° F.) | 26200 | | | | 29750 | 16600 | | 39000 |
| 135° C. (275° F.) | 7710 | 12125 | 9725 | 7500 | 8425 | 7100 | 9100 | 8750 |
| 148.9° C. (300° F.) | 4675 | 6350 | 5325 | 4525 | 5150 | 4200 | 5325 | 5375 |
| 162.8° C. (325° F.) | 3075 | 4190 | 3500 | 2980 | 3475 | 2800 | 3550 | 3375 |
| 176.7° C. (350° F.) | 2220 | 2945 | 2450 | 2080 | 2315 | 1920 | 2385 | 2275 |
| Mettler Softening Point | 121° C. | 125° C. | 125° C. | 124° C. | 120° C. | 118° C. | 118° C. | 115° C. |
| Density g-cm$^{-3}$ ASTM 792 | 0.86-0.87 | 0.86-0.87 | 0.86-0.87 | 0.86-0.87 | 0.86-0.87 | 0.86-0.87 | 0.86-0.87 | 0.86-0.87 |

These data indicates that the materials will provide excellent construction bonding in disposable absorbent articles. Note viscosity relates to the resistance to flow of the material under certain conditions. This distinctive property determines the flowability, degree of wetting, and penetration of the substrate by the molten polymer. It provides an indication of its processability and utility as a hot melt adhesive material. Melt viscosity is generally directly related to a polymer molecular weight and is reported in Millipascal-second's or centipoise (cP) using a Brookfield thermosel RVT viscometer using a rotor number 27 at the stated temperature.

Mettler softening point in degrees Centigrade or degrees Fahrenheit is typically measured using ASTM D3104. The amorphous nature of the poly olefin materials results in a melting point, which is not sharp or definite. Rather as the temperature increases, amorphous polymers gradually change from a solid to a soft and then to a liquid material. No clearly defined glass transition or melting temperature is often noted. This temperature testament that generally measures the precise temperature at which a disc of polymer sample, heated at a rate of 2° C. per minute or 10° F. per minute becomes soft enough to allow the test object, a steel ball (grams) drops through the sample. The softening point of a polymer reported in degrees Centigrade or degrees Fahrenheit is important because it typically indicates the polymer's heat resistance, useful application temperatures and solidification points.

The claims may suitably comprise, consist of, or consist essentially of, or be substantially free of any of the disclosed or recited elements. The invention illustratively disclosed herein can also be suitably practiced in the absence of any element which is not specifically disclosed herein. The various embodiments described above are provided by way of illustration only and should not be construed to limit the claims attached hereto. Various modifications and changes may be made without following the example embodiments and applications illustrated and described herein, and without departing from the true spirit and scope of the following claims.

I claim:

1. A hot melt adhesive composition consisting essentially of:
   (i) about 90 to 10 wt. % of an amorphous polyolefin copolymer composition comprising 50 to 70 wt. % 1-butene;
   (ii) about 10 to 90 wt. % of a heterophase polypropylene copolymer composition comprising propene and a comonomer comprising ethylene, 1-hexene or 1-octene and comprising amorphous blocks and crystalline blocks; and
   (iii) about 0.1 to 30 wt. % of a polyisobutylene plasticizer made with an AlCl$_3$; wherein the adhesive provides cohesive strength from the heterophase polyolefin copolymer and adhesive strength from the amorphous polypropylene copolymer.

2. The adhesive of claim 1 wherein the heterophase polyolefin copolymer comprises at least about 5 wt. % crystalline sequences or blocks.

3. The adhesive of claim 1 wherein the heterophase polypropylene copolymer comprises greater than 40 wt. % of propene and less than 60 wt. % of the comonomer and has a crystallinity of greater than 10%.

4. The adhesive of claim 1 wherein the adhesive is substantially free of a tackifier.

5. The adhesive of claim 1 wherein there is about 50 to 80 wt. % of the amorphous polyolefin copolymer and about 10 to 50 wt. % of the heterophase polypropylene copolymer.

6. An article comprising a substrate and a film, fiber, cellulose sheet or non-woven having an adhesive bond there between comprising the adhesive of claim 1 wherein the adhesive provides cohesive strength from the heterophase polypropylene copolymer and adhesive strength from the amorphous polyolefin copolymer.

\* \* \* \* \*

UNITED STATES PATENT AND TRADEMARK OFFICE
CERTIFICATE OF CORRECTION

| | |
|---|---|
| PATENT NO. | : 8,865,824 B2 |
| APPLICATION NO. | : 13/836385 |
| DATED | : October 21, 2014 |
| INVENTOR(S) | : William L. Bunnelle |

It is certified that error appears in the above-identified patent and that said Letters Patent is hereby corrected as shown below:

In the claims

Column 12, Line 60, Claim 1, "polyolefin" should be changed to -- polypropylene --.

Column 12, Line 62, Claim 1, "polypropylene" should be changed to -- polyolefin --.

Signed and Sealed this
Thirteenth Day of October, 2015

Michelle K. Lee
*Director of the United States Patent and Trademark Office*